United States Patent
Nicolau et al.

(10) Patent No.: US 8,366,933 B2
(45) Date of Patent: Feb. 5, 2013

(54) METHOD FOR BACTERIAL TREATMENT OF EFFLUENTS CONTAINING 2-ETHYLHEXYL NITRATE

(75) Inventors: Elodie Nicolau, Nantes (FR); Remy Marchal, Chatou (FR); Yves Jouanneau, Sassenage (FR)

(73) Assignees: Commissariat a l'Energie Atomique, Paris (FR); IFP Energies Nouvelles, Rueil-Malmaison Cedex (FR)

( * ) Notice: Subject to any disclaimer, the term of this patent is extended or adjusted under 35 U.S.C. 154(b) by 508 days.

(21) Appl. No.: 12/601,425

(22) PCT Filed: May 21, 2008

(86) PCT No.: PCT/FR2008/000718
§ 371 (c)(1),
(2), (4) Date: May 25, 2010

(87) PCT Pub. No.: WO2009/004154
PCT Pub. Date: Jan. 8, 2009

(65) Prior Publication Data
US 2010/0276362 A1    Nov. 4, 2010

(30) Foreign Application Priority Data
May 25, 2007  (FR) .................................... 07 03808

(51) Int. Cl.
*C02F 3/00*    (2006.01)

(52) U.S. Cl. ........................................ 210/610; 210/611
(58) Field of Classification Search ........... 210/610–611
See application file for complete search history.

(56) References Cited

U.S. PATENT DOCUMENTS
6,403,365 B1    6/2002    Solano-Serena et al.

FOREIGN PATENT DOCUMENTS
FR    2 790 752 A    9/2000

OTHER PUBLICATIONS

Bornemann, H., Scheidt, F. and Sander, W. (2002), Thermal decomposition of 2-ethylhexyl nitrate (2-EHN). Int. J. Chem. Kinet., 34: 34-38. doi: 10.1002/kin.10017.*
"International Search Report," International Application No. PCT/FR2008/000718, Date of Completion Feb. 12, 2009, Date of Mailing Feb. 23, 2009, 2 pages.

* cited by examiner

*Primary Examiner* — Chester Barry
(74) *Attorney, Agent, or Firm* — Millen, White, Zelano & Branigan, P.C.

(57) ABSTRACT

The invention relates to a method for treating effluents containing 2-ethylhexyl nitrate (2-EHN), or nitric ester of 2-ethylhexane-1-ol, in order to reduce at least partly the concentration thereof, characterized in that it comprises growing, in the presence of a suitable substrate, a *Corynebacterium urealyticum* CIP-1-2126 bacterium and degrading the 2-EHN contained in the effluents by the biomass of said bacterium thus produced. The invention has application in the Application: depollution of waters and soils polluted by 2-EHN.

16 Claims, No Drawings

METHOD FOR BACTERIAL TREATMENT OF EFFLUENTS CONTAINING 2-ETHYLHEXYL NITRATE

FIELD OF THE INVENTION

The present invention relates to a method for treating effluents containing 2-ethylhexyl nitrate (or 2-EHN) using microorganisms capable of degrading this contaminant.

The contamination of soils and aquifers by petroleum products and derivatives thereof is an important problem and knowing the biodegradability of these organic pollutants is an obvious challenge.

The method according to the invention applies particularly to the industries for treatment of waters and soils contaminated by diesel fuel.

BACKGROUND OF THE INVENTION

Alkyl nitrates are added to commercial diesel fuels in order to guarantee their cetane number (Suppes et al., Energy & Fuels 15, 151-157, 2001). The cetane number is an auto-ignition characteristic of diesel fuels. According to engine manufacturers, a cetane number of 50 is an acceptable minimum value for combustion to be controlled satisfactorily. In the case of direct-injection engines, the cetane number also conditions the noise delivered by the engine (Guibet J. C. et al., Carburants et Moteurs, Editions Technip, Paris (1999)).

2-EHN is the most commonly used procetane additive. Liquid at ambient temperature, this compound decomposes autocatalytically above 100° C., releasing free radicals that reduce the auto-ignition delay of the engine. 2-EHN is added to fuels in a proportion of 300 to 1000 mg/L, which explains why $10^5$ tons of this compound are produced yearly worldwide. 2-EHN is the most commonly used procetane additive.

2-EHN is the nitric ester of a branched alcohol, 2-ethylhexanol. Its structure is as follows:

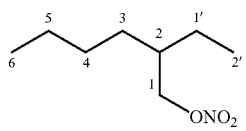

Its main physico-chemical properties are given in Table 1.

TABLE 1

Main physico-chemical properties of 2-EHN*

| Characteristic | Value |
| --- | --- |
| CAS number | 27247-96-7 |
| Molar mass | 175.2 g |
| Density | 0.96 kg/L |
| Vapour pressure at 20° C. | 27 Pa |
| Solubility at 20° C. | 12.6 mg/L |
| Log $K_{O/W}$ | 5.24 |

*According to "The American Chemistry Council Petroleum Additives Panel Health, Environmental and Regulatory Task Group", October 2006

Diesel fuel is 88% biodegradable by the microflora of soils polluted by hydrocarbons (Penet et al., Appl. Microbiol. Biotechnol., 66, 40-47, 2004). However, the acceptability of 2-EHN is a topical issue, especially within the context of the European directive REACH (Chemical Consulting Global Laboratory Network). In fact, no data relative to the biodegradability of 2-EHN is available.

On the other hand, the ecotoxicity properties of 2-EHN are known. The acute toxicity of 2-EHN is low since the LC50 (50% lethal concentrations) for zebrafish and Daphnia are higher than its water solubility. However, 2-EHN is much more dangerous when administered in repeated doses. In rats, the level at which no unfavourable effect is observed after 28 days (No Observed Adverse Effect Level or NOAEL) is only 28 mg/kg·day (Someroja et al., Toxicol. Lett., 19, 189-93, 1983). This result shows that the biodegradability of 2-EHN is a key parameter as regards global risk in case of accidental release. In fact, biodegradability determines the critical time of exposure to the dangerous molecule.

Sturm's test (Sturm, Journal of Oil Chemistry Society, 50, 159-167, 1973) is the most commonly used normalized test for determining the biodegradation of a compound. This test, carried out in a liquid medium, is fast and easy to conduct. It is performed in a closed system where the compound to be tested is subjected to the cellular biomass consisting of a sewage disposal plant sludge. The degradation is then measured by means of the final production of $CO_2$ trapped by a base. According to Battersby et al. (Chemosphere, 38, 3219-3235, 1999), Sturm's test is applicable only to the water-soluble organic products of low volatility. The biodegradability test corresponding to that of the $CO_2$ headspace was used for 2-EHN. This test showed that 2-EHN is not readily biodegradable according to the usual criteria that impose 60% biodegradation within 28 days with, at least, 10% biodegradation within 10 days. According to the authors of a report from the American Chemistry Council (2006) concerning 2-EHN, the absence of biodegradability therefore has to be attributed to the volatility of the substrate. Considering the small amounts of substrate used in this normalized test, the initial 2-EHN used as substrate is mainly located in the headspace of the test jar and it is then not available for the microflora. This test is therefore not pertinent for 2-EHN.

It is known that substituted hydrocarbons often show reluctance to biodegradation. 2-EHN has a branched structure and it is consequently not or very poorly degraded by the sewage disposal plant microflora that are conventionally used in biodegradation tests.

We have discovered a bacterium allowing to degrade 2-EHN and adapted a test allowing to measure the biodegradability of this compound.

SUMMARY OF THE INVENTION

The present invention describes a method for treating hydrocarbon-containing effluents comprising 2-EHN, wherein a Corynebacterium urealyticum CIP-I-2126 bacterium is grown in the presence of a suitable substrate and the 2-EHN contained in the effluents is at least partly degraded by the biomass of said bacterium thus produced.

One of the objects of the invention is to describe a method using this bacterium in order to degrade this compound in aqueous effluents so that the discharges are compatible with the standards in force.

Another object of the invention is the use of this bacterium for in-situ decontamination of polluted waters and soils.

DETAILED DESCRIPTION

The method for treating hydrocarbon-containing effluents comprising 2-EHN according to the present invention uses a bacterium filed at the Institut Pasteur (Collection Nationale de Cultures des Micro-organismes de l'Institut Pasteur, 25 rue du Docteur Roux 75724 Paris Cedex 15, France) under the name Corynebacterium urealyticum CIP-I-2126, after an identification using the commercial chemotaxonomic test API Coryne (Biomerieux, Marcy l'Etoile, France). However, the 16S DNA sequence of the microorganism (access number: AF190800) is identical to that of the reference strain of *Mycobacterium austroafricanum*.

The bacterium according to the invention was first selected in ground water polluted by a gasoline prior to being seeded in the presence of said 2-EHN-containing effluent.

The culture medium used for growing the bacteria is a mineral salts-vitamin medium (MMSV medium) and a carbon-containing substrate that is the carbon and energy source. The carbon source is introduced either before autoclave treatment or upon seeding.

According to a characteristic of the method, the growth substrate can comprise said effluents containing 2-EHN.

According to a variant, the growth substrate can be selected from the group consisting of hydrocarbons with 5 to 16 carbon atoms, alcohols, carboxylic mono- or diacids in form of their alkali metal salts such as acetate or succinate salts, or some detergents whose hydrophobic part is made up of a linear carbon chain such as Tween® 80 (polyoxyethylene sorbitan monooleate also known as Polysorbate 80, CAS No. 9005-65-6).

The substrate is preferably selected from among Tween® 80, iso-octane, acetate or succinate of an alkali metal salt, glycerol, ethanol and mixtures thereof.

According to a preferred embodiment, in order to increase the growth rate of *Corynebacterium urealyticum* CIP-I-2126 on 2-EHN, a preculture is performed, preferably on Tween® 80, followed by cell washing, prior to seeding the saline medium containing 2-EHN as the single growth substrate.

The effluent can also be enriched in growth substrate, for example with Tween® 80.

According to another characteristic of the invention, the 2-EHN concentration in the liquid effluents is at most 12 mg/L, and it preferably ranges between 6 and 10 mg/L.

The effluents can also contain hydrocarbons belonging to the gas oil cut.

Advantageously, the *C. urealyticum* CIP-I-2126 strain has the capacity of degrading 2-EHN in the presence of a non-biodegradable hydrophobic liquid phase used as a reservoir for the substrate. This solvent phase thus attenuates the solubilized concentration in the medium. As it is being consumed, the substrate is transferred from the solvent phase to the culture medium. Inhibition through excess substrate concentration is thus avoided. Preferably, the non-biodegradable liquid phase is selected from among 2,2,4,4,6,8,8-heptamethylnonane (HMN) and silicone oil.

2-EHN can be advantageously used as nitrogen source for the microorganism.

Evaluation of the biodegradability is carried out by calculating the degradation rate of the 2-EHN and the mineralization yield.

The degradation rate of 2-EHN is defined as the molar fraction of 2-EHN consumed by the culture.

The mineralization yield is defined as the ratio of the number of final moles of carbon released in form of $CO_2$ to the number of moles of carbon of 2-EHN introduced.

The ex-situ techniques of biological pollution clean-up relate to soils and subsoil water. The treatment of soils involves conventional or trickling biofilter techniques. In these biofilters, the bacteria are attached to a mineral or organic support, or they can be added as an inoculum to sewage plant sludge. The effluents can be enriched in growth substrate (Tween® 80 for example) to improve the growth of the strain.

According to an embodiment, the strain according to the invention can be used in situ in a biobarrier. The microorganisms cultured in reactors are attached to a solid support (peat granules, perforated stainless steel plates) arranged inside a trench located on the route of the pollution plume, preferably perpendicular to the route. Oxygen is provided by injection of air into the trench. The pollutant is degraded as it passes through the biobarrier.

Other features of the invention will be clear from reading the examples hereafter that illustrate the invention.

Example 1 (According to the Invention)

Isolation of Strains that Degrade 2-EHN

The isolation method is essential to obtain a strain that degrades 2-EHN.

Water samples taken from a ground water formerly polluted by a gasoline cut are used to seed, at an inoculation rate of 10% (v/v), hermetically sealed flasks containing a mineral salts-vitamin medium (MMSV medium) whose composition is as follows:

| | |
|---|---|
| $Na_2HPO_4, 12H_2O$ | 4.5 g/L |
| $NH_4NO_3$ | 1.0 g/L |
| $KH_2PO_4$ | 680 mg/L |
| $MgSO_4, 7H_2O$ | 100 mg/L |
| $FeSO_4, 7H_2O$ | 1 mg/L |
| $MnSO_4, H_2O$ | 100 µg/L |
| $(NH_4)_6Mo_7O_{24}, H_2O$ | 25 µg/L |
| $NaB_4O_7, 10H_2O$ | 25 µg/L |
| $Co(NO_3)_2, 6H_2O$ | 25 µg/L |
| $CuCl_2$ | 25 µg/L |
| $ZnCl_2$ | 25 µg/L |
| $NH_4NO_3$ | 10 µg/L |
| biotin | 200 µg/L |
| pyridoxine | 100 µg/L |
| riboflavin | 50 µg/L |
| nicotinamic acid | 50 µg/L |
| panthotenate | 50 µg/L |
| p-aminobenzoic acid | 50 µg/L |
| lipoic acid | 50 µg/L |
| folic acid | 20 µg/L |
| thiamine | 15 µg/L |
| cyanocobalamine | 1.5 µg/L |

Immediately after seeding, the growth substrate, a substituted alkane, iso-octane (or 2,2,4-trimethylpentane), is added to the MMSV medium in a proportion of 500 mg/L. The iso-octane advantageously allows to enrich the bacterial population in microorganisms capable of degrading the 2-EHN because it is a substituted hydrocarbon that has lower inhibiting properties than 2-EHN.

After three-week incubation under stirring at 30° C., it appears that the absorbance of the enrichment culture has increased by about 0.1 unit. A first transplanting in a medium of identical composition is then carried out, with the same seeding rate as for the enrichment culture. When a growth is observed again by means of an absorbance increase, a second transplanting is performed under the same conditions as above.

After two-week incubation, an aliquot part of the liquid culture medium is then taken and spread on Petri dishes of gelosed MMSV medium. These dishes are incubated in a closed enclosure and iso-octane is supplied in vapour form by placing in the enclosure a test tube containing some milliliters of pure iso-octane. After two-week incubation at 30° C., colonies observed at the surface of the gelosed medium are isolated. They are capable of degrading 2-EHN.

After a preculture on Tween® 80 and cell washing, the MMSV medium containing 2-ethylhexyl nitrate in a proportion of 500 mg/L as the single growth substrate is seeded.

After three-week incubation under stirring at 30° C., an increase in the cellular biomass (94 mg/L) and a net $CO_2$ production (115 mg/L) are observed.

Among the many strains tested, only the *C. urealyticum* CIP-I-2126 strain, isolated from a ground water contaminated by a gasoline, is capable of degrading the 2-EHN under these culture conditions. Many samples have to be treated to isolate an active strain, which shows that active strains are relatively rare in the environment.

Determining the Degradation Capacity for 2-EHN

We used the following test to assess simply and quantitatively the capacity for degradation of 2-EHN of the *C. urealyticum* CIP-I-2126 strain:

A 120-mL penicillin flask, hermetically sealed and containing 10 mL of MMSV medium to which 486 mg/L 2-EHN were added, is seeded with the CIP-I-2126 strain. The culture is put under stirring (150 rpm) at a temperature of 30° C. for 28 days. The residual 2-EHN of the flasks is measured after methylethyl ether (MTBE) extraction and gas chromatography (GC) separation on a PONA column (Chrompack) under flame ionization detection.

Concurrently with the residual substrate measurement, the amount of $CO_2$ produced during the test is monitored by chromatography while taking samples of aliquot fractions (250 µL) of the flask headspace. The gaseous sample taken is injected into a chromatograph equipped with a Porapak column (Millipore Corp.) and provided with a catharometric detector. The $CO_2$ produced is assessed by means of an external standard. The 2-EHN degradation rate and the mineralization yield are calculated. The results obtained with the CIP-I-2126 strain are shown in Table 1.

TABLE 1

Kinetic monitoring of the degradation of 2-EHN by the CIP-I-2126 strain

| INCUBATION TIME (DAYS) | DEGRADATION RATE (%) |
|---|---|
| 0 | 0 |
| 8 | 35 |
| 10 | 40 |
| 12 | 63 |
| 14 | 70 |
| 15 | 91 |
| 20 | 100 |
| 28 | 100 |

It can be seen that the *C. urealyticum* CIP-I-2126 strain can degrade all of the 2-EHN introduced. At the end of the test, 20% of the carbon were mineralized to $CO_2$. The carbon that is not mineralized is notably used for the production of cellular biomass.

Identification of the CIP-I-2126 Strain

The CIP-I-2126 strain that has the capacity of degrading 2-EHN was subjected to biochemical tests in order to be identified by its phenotypical characters.

The CIP-I-2126 strain is a strict aerobic Gram-positive bacillus, non-mobile, non-sporulated, non-capsulated and unbranched. The biochemical characters for identification are as follows:

Strict Aerobic Respiratory Metabolism
catalase+
oxydase−
reductase nitrate−
reductase nitrite−
urea+
esculin−
Tween-80-esterase+

API Coryne gallery positive characters: α-glucosidase, urea, catalase.

The biochemical characters expressed confirm that the CIP-I-2126 strain belongs to the *Corynebacterium urealyticum* species.

Example 2 (Comparative)

Activated sludge samples taken in an urban sewage disposal plant are used to carry out strain isolations under the same conditions as those described in Example 1.

After three-week incubation, none of the seven bacterial isolates is capable of degrading 2-EHN.

Example 3

Effect of the 2-EHN Concentration

The *Corynebacterium urealyticum* CIP-I-2126 strain is cultured under the same temperature and stirring conditions as in Example 1, but in the presence of the following 2-EHN concentrations: 238, 486, 1150 and 2310 mg/L. The 2-EHN degradation rates in the various tests are given in Table 2.

TABLE 2

Influence of the 2-EHN concentration on degradation

| INITIAL 2-EHN CONTENT (MG/L) | TIME | DEGRADATION RATE (%) |
|---|---|---|
| 238 | 28 days | 100 |
| 486 | 28 days | 100 |
| 1150 | 28 days | 50 |
| 2310 | 28 days | 16 |

Table 2 shows that the *C. urealyticum* CIP-I-2126 strain is capable of degrading 2-EHN over 100% up to at least a concentration of 486 mg/L. Besides, the strain withstands a 2.3 g/L concentration of 2-EHN in the medium but degradation is then incomplete (Table 2).

Example 4

Degradation Capacity in the Presence of a Non-Biodegradable Liquid Phase

The capacity for degradation of 2-EHN by the *C. urealyticum* CIP-I-2126 strain in the presence of a non-biodegradable hydrophobic liquid phase used as a substrate reservoir is studied. The cultures were carried out at 30° C. with a respirometer so as to determine the kinetic characteristics of the biodegradation.

Two non-biodegradable liquid phases were tested: 2,2,4,4, 6,8,8-heptamethylnonane (HMN) and silicone oil (Table 3).

TABLE 3

2-EHN degradation by the *C. urealyticum* CIP-I-2126
strain in the presence of a hydrophobic phase

| LIQUID PHASE ADDED | DEGRADATION RATE (%) | BIODEGRADATION TIME (DAYS) | MAXIMUM* DEGRADATION RATE (MMOLO$_2$/J) |
|---|---|---|---|
| none | 100 | 20 | 0.3 |
| HMN | 100 | 10 | 5.3 |
| Silicone oil | 100 | 10 | 5.8 |

*The maximum degradation rate is expressed in mmol of O$_2$ consumed per day per flask containing 500 mL medium at 500 mg/L 2-EHN.

Table 3 shows that the *C. urealyticum* CIP-I-2126 strain degrades 2-EHN even faster when it is introduced in a non-biodegradable liquid phase. This phase decreases the 2-EHN concentration at equilibrium in the aqueous phase and it reduces the inhibiting effect of the dissolved 2-EHN.

Example 5

Degradation Capacity of the 2-Ethylhexanol Involved in the Preparation of 2-EHN and of Mono- and Di-2 Ethylhexyl Phthalates Tests were carried out to study the capacity of the *C. urealyticum* CIP-I-2126 strain to degrade 2-ethylhexanol in the presence of a non-biodegradable hydrophobic liquid phase used as substrate reservoir, 2,2,4,4,6,8,8-heptamethylnonane (HMN).

Di-2-ethylhexyl phthalate (DEHP) belongs to the family of phthalic acid esters. DEHP is used as a plasticizer in polyvinyl chloride (PVC) to provide flexibility, temperature resistance and tolerance of the materials. As it is widely used, DEHP is found as a contaminant in drinking water, sewage water and sediments. In the environment, hydrolysis of DEHP yields phthalic acid whose biodegradability is widely known and 2-ethylhexanol. 2-ethylhexanol is more reluctant and it accumulates as such or in the environment in form of its oxidation product, 2-ethylhexanoic acid (Nakamiya et al. J. Biosc. Bioeng. 99, 115-119 (2005) and Chen et al. Appl. Microbiol. Biotech. 74, 676-682, 2007). Now, hydrolysis of the nitrate group of 2-EHN can also lead to the formation of 2-ethylhexanol. The degradation of this intermediary has therefore been tested.

The cultures were conducted at 30° C. in penicillin flasks, the production of CO$_2$ was measured by GC under catharometric detection. The residual 2-ethylhexanol was extracted with MTBE, then determined by GC/FID after 28 days of degradation by the strain. The degradation of 2-ethylhexanol by the *C. urealyticum* CIP-I-2126 strain is 100%. The mineralization yield of the 2-ethylhexanol to CO$_2$ is 20%.

The invention claimed is:

1. A method for treating effluents comprising 2-ethylhexyl nitrate (2-EHN), wherein a *Corynebacterium urealyticum* CIP-I-2126 bacterium is grown in the presence of a suitable substrate and the 2-EHN contained in the effluents is at least partly degraded by the biomass of said bacterium thus produced.

2. A method as claimed in claim 1, wherein the bacterium is first selected in ground water formerly polluted by a gasoline prior to being seeded in the presence of said 2-EHN-containing effluent.

3. A method as claimed in claim 1, wherein the substrate comprises said 2-EHN-containing effluents.

4. A method as claimed in claim 1, wherein the substrate is selected from the group consisting of hydrocarbons with 5 to 16 carbon atoms, alcohols, carboxylic mono- or diacids and their alkali metal salts, and mixtures thereof.

5. A method as claimed in claim 4, wherein the substrate is selected from among polyoxyethylene sorbitan monooleate (Tween® 80 ), iso-octane, acetate or succinate of an alkali metal salt, glycerol, ethanol and mixtures thereof.

6. A method as claimed in claim 1, wherein a preculture is performed, followed by cell washing, prior to seeding a saline medium containing 2-EHN as a single growth substrate.

7. A method as claimed in claim 4, wherein the growth substrate is enriched with said Tween® 80.

8. A method as claimed in claim 1, wherein the 2-EHN concentration in the liquid effluents is at most 12 mg/L.

9. A method as claimed in claim 1, wherein the 2-EHN is degraded in the presence of a non-biodegradable liquid phase used as a reservoir for the substrate.

10. A method as claimed in claim 9, wherein said non-biodegradable liquid phase is selected from among 2,2,4,4,6,8,8-heptamethylnonane (HNM) and silicone oil.

11. A method as claimed in claim 1, wherein the 2-EHN is used as a nitrogen source.

12. A method as claimed in claim 1, wherein the effluents contain a gas oil cut.

13. A method as claimed in claim 1, wherein said bacterium is developed on a system of at least one biofilter, the effluents are fed into the biofilter and the effluent at least partly freed of 2-EHN is discharged.

14. A method as claimed in claim 13, wherein the bacteria are attached to a mineral or organic support, or they are added as an inoculum to sewage plant sludge.

15. A method as claimed in claim 1, wherein said bacterium is developed on a solid support arranged inside a trench perpendicular to the route of the polluted effluent forming a biobarrier, and oxygen is provided by injection of air into the trench, the 2-EHN pollutant being degraded as it passes through the biobarrier.

16. A method according to claim 8, wherein the concentration of 2-EHN is between 6 and 10 mg/l.

* * * * *

UNITED STATES PATENT AND TRADEMARK OFFICE
CERTIFICATE OF CORRECTION

PATENT NO. : 8,366,933 B2  Page 1 of 1
APPLICATION NO. : 12/601425
DATED : February 5, 2013
INVENTOR(S) : Nicolau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this
First Day of September, 2015

Michelle K. Lee
*Director of the United States Patent and Trademark Office*